United States Patent
Fang et al.

(10) Patent No.: US 12,247,198 B2
(45) Date of Patent: Mar. 11, 2025

(54) NUCLEIC ACID SYNTHESIS AND PURIFICATION DEVICE, USE THEREOF, AND NUCLEIC ACID SYNTHESIS AND PURIFICATION METHOD

(71) Applicant: BGI SHENZHEN, Guangdong (CN)

(72) Inventors: Xin Fang, Guangdong (CN); Xiaoluo Huang, Guangdong (CN); Yue Shen, Guangdong (CN); Xun Xu, Guangdong (CN)

(73) Assignee: BGI SHENZHEN, Guangdong (CN)

( * ) Notice: Subject to any disclaimer, the term of this patent is extended or adjusted under 35 U.S.C. 154(b) by 625 days.

(21) Appl. No.: 17/311,697

(22) PCT Filed: Dec. 14, 2018

(86) PCT No.: PCT/CN2018/121092
§ 371 (c)(1),
(2) Date: Jun. 8, 2021

(87) PCT Pub. No.: WO2020/118655
PCT Pub. Date: Jun. 18, 2020

(65) Prior Publication Data
US 2022/0025354 A1 Jan. 27, 2022

(51) Int. Cl.
*C12N 15/10* (2006.01)
*B01J 19/00* (2006.01)

(52) U.S. Cl.
CPC .......... *C12N 15/10* (2013.01); *B01J 19/0046* (2013.01); *B01J 2219/00497* (2013.01); *B01J 2219/00759* (2013.01)

(58) Field of Classification Search
CPC ............ C12N 15/10; B01J 2219/00497; B01J 2219/00277
See application file for complete search history.

(56) References Cited

U.S. PATENT DOCUMENTS

| | | | |
|---|---|---|---|
| 5,904,848 A * | 5/1999 | Wong | B01J 20/28026 210/500.36 |
| 9,309,556 B2 | 4/2016 | Myllykangas et al. | |
| 10,072,283 B2 | 9/2018 | Myllykangas et al. | |
| 2012/0157322 A1 | 6/2012 | Myllykangas et al. | |
| 2015/0017635 A1 | 1/2015 | Myllykangas et al. | |
| 2019/0024141 A1 | 1/2019 | Myllykangas et al. | |

FOREIGN PATENT DOCUMENTS

| CN | 103228798 A | 7/2013 | | |
|---|---|---|---|---|
| CN | 204151332 U | 2/2015 | | |
| CN | 107383246 A | 11/2017 | | |
| CN | 207483713 U | 6/2018 | | |
| EP | 3284851 A1 | 2/2018 | | |
| WO | WO-0210373 A2 * | 2/2002 | .......... | C12N 15/101 |
| WO | WO-2016193282 A1 * | 12/2016 | .......... | B01D 15/203 |

OTHER PUBLICATIONS

Laurent, A., et al. Tetrahedron Letters. 45, 2004, 8883-8887. (Year: 2004).*
Chinese Patent Office, First Office Action issued Nov. 29, 2023, for corresponding Chinese Patent Application No. 201880099717.2 (English translation provided).
Farre et al., Automated Oligonucleotide Solid-Phase Synthesis on Nanosized Silica Particles Using Nano-on-Micro Assembled Particle Supports, Langmuir Article, American Chemical Society, Langmuir 2010, 26(7), pp. 4941-4950.
Pon, Solid-Phase Supports for Oligonucleotide Synthesis, Synthesis of Unmodified Oligonucleotides, Current Protocols in Nucleic Acid Chemistry (2000), Unit 3-1, pp. 3.1.1-3.1.28.
Pon, Attachment of Nucleosides to Solid-Phase Supports, Synthesis of Unmodified Oligonucleotides, Current Protocols in Nucleic Acid Chemistry (2000), Unit 3-2, pp. 3.2.1-3.2.23.
Ding Xiandong, et al., Development of the Stationary Phases Based on Controlled Pore Glass Used for High Performance, A Journal of Analytical Chemistry, May 1, 1993, pp. 410-415, No. 4, English Abstract.
Richard T. Pon, et al., Linker phosphoramidite reagents for the attachment of the first nucleoside to underivatized solid-phase supports, Nucleic Acids Research, Jan. 29, 2004, pp. 623-631, vol. 32, No. 2, Oxford University Press.
State Intellectual Property Office of People's Republic of China, Notice of Decision of Granting Patent Right for Invention (PCT Application Entering National Phase), dated Oct. 29, 2024.

* cited by examiner

*Primary Examiner* — Eric Olson
*Assistant Examiner* — Samuel L Galster
(74) *Attorney, Agent, or Firm* — Duane Morris LLP (57) ABSTRACT

A nucleic acid synthesis device and a nucleic acid purification device, uses thereof, and a nucleic acid synthesis method and a nucleic acid purification method. The nucleic acid synthesis device includes a solid support, and the solid support includes a controlled pore glass (CPG), the CPG is an unmodified and bare CPG, a surface of the CPG has a hydroxyl group, and the hydroxyl group is attachable, though a covalent bond, to a phosphoramidite-protected nucleotide monomer or multimer for synthesis of nucleic acid. The nucleic acid synthesis device of the present disclosure can be used for not only synthesis of an oligonucleotide primer, but also for purification of enzymatic digestion and PCR product by using the oligonucleotide primer immobilized on the CPG, and has advantages of simple structure, small volume, light weight, high efficiency, low costs, and diversified functions.

12 Claims, 4 Drawing Sheets

NUCLEIC ACID SYNTHESIS AND PURIFICATION DEVICE, USE THEREOF, AND NUCLEIC ACID SYNTHESIS AND PURIFICATION METHOD

TECHNICAL FIELD

The present disclosure relates to the technical field of nucleic acid synthesis, and particularly, to a nucleic acid synthesis device, a nucleic acid purification device, uses thereof, a nucleic acid synthesis method, and a nucleic acid purification method.

BACKGROUND

The classic DNA synthesis column includes a solid support, a screen plate, and a hollow column tube. The solid support typically uses a controlled pore glass (CPG). The CPG has many irregular internal pore canals, and has a large pore network. A size of the pore canal is also referred to as a pore size, and the CPG has stable pore size. Generally, CPG having a pore size of 500 Angstroms (Å) to 1000 Å is selected for DNA synthesis, and other pore sizes can be selected as well. The screen plate is typically formed by sintering ultra-high molecular weight polyethylene (UHMW-PE) or high-density polyethylene (HDPE) powders. In the DNA synthesis columns, the screen plate is configured to block CPG from leaking down and to allow synthesis reagents to pass through. The hollow column tube is injection molded from polypropylene.

The second-generation DNA universal synthesis column consists of a Controlled Pore Glass Frit (CPG Frit) and a hollow column tube. The CPG Frit is formed by sintering CPG and UHMW-PE or HDPE powder. The PE particles encase and immobilize the CPG spheres. The PE particles are bridged to form a certain pore size, and the CPG spheres are uniformly embedded in a rigid network structure formed by the PE bridges to form a screen plate with a certain pore size and porosity. During a primer synthesis, the synthesis reagent flows through the internal pore canals of CPG and the pore canals formed by the PE bridges, which ensures a sufficient length of the flow path of the reagent, thereby prolonging the duration of the chemical reaction and increasing the opportunity for the reactants to contact reaction sites on the CPG. The CPG spheres are immobilized by the encapsulation effect of the polymer, and thus they cannot be rotated due to the flow of reagent, which further prolongs the contact time between reagent and reaction sites on the CPG, thereby improving synthesis efficiency and product purity.

At present, oligonucleotides such as primers are commonly synthesized using the second-generation CPG Frit synthesis columns, in which CPG is made of silica and is widely used as a support for solid-phase synthesis of oligonucleotides. The CPG is typically ligated with a universal linker modification having chemical groups. The synthesis is initiated by removing a DMT protecting group on the linker to which the CPG is attached using trichloroacetic acid (TCA), to obtain the free 5'-hydroxyl group for the next condensation reaction with phosphoramidite monomer. After the reaction, the oligonucleotide ligated to the CPG is cleaved through aminolysis and purified for use in subsequent experiments. However, the oligonucleotide cannot be immobilized. Due to the super hydrophobicity of the adopted PE material, which encases CPG, this type of synthesis column is unable to absorb the reaction solution of enzyme digestion, PCR, and the like.

The separation and purification of DNA is a critical step in molecular biology procedures, and the separated DNA can be used for downstream gene cloning, probe preparation, and other experiments. The separation and purification of DNA generally includes two types: 1) extraction of total DNA, such a separation and purification only needs to remove other impurities in the tissues, cells, or in vitro DNA synthesis reaction products, and then isolate all the required DNA genetic material by physical or chemical methods; and 2) extraction of specific DNA, such a separation and purification usually requires to extract specific DNA in tissues, cells, or amplified products of in vitro DNA synthesis in accordance with the purpose of the experiments, the specific DNA including a certain functional type of DNA (such as plasmid DNA), a certain length of DNA, or a certain sequence of specific DNA.

DNA separation and purification methods commonly used in laboratories include silica gel membrane centrifugal adsorption column method and magnetic bead adsorption method. The core principles of these two methods are similar. Both of them use the groups bonded on the surface of silica gel membranes or magnetic beads to adsorb the charges on the surface of the DNA under certain buffer conditions, so as to separate and purify the target DNA. Both of these methods have been developed into mature commercial kits and are commercially available. As an example, TIANGEN's Universal DNA Purification Recovery Kit employs a unique buffer system and a centrifugal adsorption column to recover DNA fragments from TAE or TBE agarose gel and to directly purify PCR products, while removing impurities such as proteins, other organic compounds, inorganic salt ions, and oligonucleotide primers, thereby meeting various experimental needs. The sol solution contains a pH indicator, and the sol state can be judged based on the color. The principle of the gel recovery kit is as follow: the gel blocks are rapidly melted in the gel melting solution and DNA is released, the DNA fragments are selectively adsorbed on a silica gel membrane after adding a high chaotropic sequence solution, the impurities and high concentration of salt ions remaining on the silica gel membrane are washed with a rinsing solution, and then the DNA fragments adsorbed to the silica gel membrane are eluted with an elution buffer or water to be used in various molecular biology experiments. The magnetic bead adsorption nucleic acid extraction uses superparamagnetic silica nanomagnetic beads, which are prepared by improving and modifying the surface of superparamagnetic nanoparticles with nanotechnology. The magnetic beads are capable of specifically recognizing and efficiently binding to nucleic acid molecules on microscopic interfaces. By utilizing the superparamagnetism of the silica nanospheres, DNA and RNA can be isolated from samples such as blood, animal tissues, food, pathogenic microorganisms, etc. under the action of Chaotropic salts (guanidine hydrochloride, guanidine isothiocyanate, etc.) and an external magnetic field. Thus, the magnetic bead adsorption nucleic acid extraction can be used in clinical disease diagnosis, blood transfusion safety, forensic identification, environmental microorganism detection, food safety detection, molecular biology research, and other fields.

DNA recovery methods commonly used in laboratories are relatively costly, and the operating procedures thereof are cumbersome and complicated procedure. Thus, they cannot purify specific DNA sequences, and require the use of buffers containing toxic chemical reagents.

SUMMARY

The present disclosure provides a nucleic acid synthesis device and a nucleic acid purification device, uses thereof, and methods for nucleic acid synthesis and purification. The nucleic acid synthesis device can be used not only for synthesis of oligonucleotide sequences, but also for purification of enzymatic digestion products, PCR products, and the like by using the oligonucleotide sequences immobilized on CPG, having the advantages of simple structure, small volume, light weight, high efficiency, low costs, and diversified functions. The nucleic acid purification device is capable of purifying a specific nucleic acid sequence, and has the advantage such as efficient, fast, convenient, safe and non-toxic.

According to a first aspect, an embodiment provides a nucleic acid synthesis device including a solid support. The solid support includes a controlled pore glass (CPG), the CPG is an unmodified and bare CPG, a surface of the CPG has a hydroxyl group, and the hydroxyl group is attachable, though a covalent bond, to a phosphoramidite-protected nucleotide monomer or multimer for synthesis of nucleic acid.

It is well known to those skilled in the art that the synthesis of oligonucleotide commonly employs the second-generation CPG Frit synthesis columns, where the CPG is a silica material, and the surface of CPG usually carries modifications of universal linker having chemical groups such as etc. However, in the present disclosure, the CPG is an unmodified and bare CPG, i.e., the CPG surface is rich in silyl groups and that the CPG surface is not modified with any chemical groups such as universal linker.

In a preferred embodiment, the nucleic acid is DNA, and accordingly the nucleic acid synthesis device is a DNA synthesis device.

In a preferred embodiment, a pore size of the CPG ranges from 500 angstroms (Å) to 2000 Å.

In a preferred embodiment, the nucleic acid synthesis device further comprises a screen plate; the screen plate includes an upper screen plate and a lower screen plate; and the CPG is disposed between the upper screen plate and the lower screen plate.

In a preferred embodiment, the upper screen plate is hydrophilically treated or selected from hydrophilic materials, and the lower screen plate is selected from hydrophobic materials.

In a preferred embodiment, the solid support further includes a thermoplastic polymer resin, and the thermoplastic polymer resin is sintered with the CPG to form a Controlled Pore Glass Frit (CPG Frit).

In a preferred embodiment, the thermoplastic polymer resin is selected from polyethylene, and preferably ultra-high molecular weight polyethylene (UHMW-PE) or high-density polyethylene (HDPE).

In a preferred embodiment, a temperature for the aforementioned sintering is 160° C. to 250° C., and preferably 180° C.

In a preferred embodiment, the CPG Frit has a diameter smaller than or equal to 3.5 mm and a thickness greater than or equal to 1.5 mm.

In a preferred embodiment, the diameter of the CPG Frit is 3 mm and the thickness of the CPG Frit is 4 mm.

In a preferred embodiment, the CPG Frit contains 0.1 to 10 mg of CPG, and preferably 4 mg of CPG.

In preferred embodiments, the CPG Frit is a hydrophilic CPG Frit.

In a preferred embodiment, the hydrophilic CPG Frit is a CPG Frit obtained by hydrophilic treatment.

In a preferred embodiment, the hydrophilic treatment includes: wetting with an alcoholic solvent, and bonding to a surfactant.

In a preferred embodiment, the alcoholic solvent is a C1-10 linear or branched alcoholic solvent, preferably methanol, ethanol, propanol, n-butanol, ethylene glycol, glycerol, and aqueous solvents or combinations thereof, and more preferably 95% (v/v) ethanol;

the surfactant is an anionic surfactant, a cationic surfactant, a zwitterionic surfactant, or a nonionic surfactant, and preferably sodium lauryl sulfate, benzalkonium bromide, polysorbate, fatty acid sorbitan, a quaternized compound, lecithin, amino acid, or combinations thereof.

In a preferred embodiment, the nucleic acid synthesis device further includes a receiving device, and the solid support is disposed in the receiving device.

In a preferred embodiment, the receiving device is a hollow column tube.

In a preferred embodiment, at least one assembly site is provided within the hollow column tube, the assembly site defines a cylinder, the solid support is in a shape of a cylinder, the solid support tangentially fits the assembly site, and a height of the assembly site is greater than a thickness of the solid support.

In a preferred embodiment, the hollow column tube has a column length of 70 mm; an inner diameter of the hollow column tube is 4.52 mm at an upper portion of the hollow column tube and reduces to 3 mm at an upper side of the assembly site, and the inner diameter of the hollow column tube is 2.95 mm at the assembly site; and a height of the assembly site is 5 mm.

According to a second aspect, an embodiment provides a nucleic acid synthesis apparatus, which includes a nucleic acid synthesis device according to the first aspect.

According to a third aspect, an embodiment provides a use of the nucleic acid synthesis device of the first aspect in nucleic acid synthesis.

In a preferred embodiment, the above nucleic acid synthesis is performed using a solid-phase phosphoramidite triester method.

According to a fourth aspect, an embodiment provides a nucleic acid synthesis method, comprising: synthesizing a nucleic acid using the nucleic acid synthesis device of the first aspect or the nucleic acid synthesis apparatus of the second aspect, in which the hydroxyl group on the surface of the CPG in the nucleic acid synthesis device is a synthesis initiation point of the nucleic acid to be synthesized and is bonded to the phosphoramidite-protected nucleotide monomer or multimer through a covalent bond.

In preferred embodiments, the above method is a solid-phase phosphoramidite triester method.

According to a fifth aspect, an embodiment provides a nucleic acid purification device, including a solid support. The solid support includes a controlled pore glass (CPG), the CPG is an unmodified and bare CPG, a surface of the CPG has a hydroxyl group, and the hydroxyl group is attached to, though a covalent bond, to a fragment of an oligonucleotide sequence, wherein the fragment of oligonucleotide sequence is specifically complementary paired or randomly paired with all of or a part of a nucleic acid to be purified.

In preferred embodiments, the fragment of oligonucleotide sequence is specifically complementary paired or randomly paired with all of or part of a regional fragment at a 3'-end or/and 5'-end of the nucleic acid to be purified.

In preferred embodiments, the length of the above oligonucleotide sequences is 6 to 12 bases in length.

In a preferred embodiment, the nucleic acid to be purified is DNA, and the nucleic acid purification device is a DNA purification device.

In a preferred embodiment, the nucleic acid to be purified is a biological reaction product, preferably an enzymatic digestion product or a PCR product.

In a preferred embodiment, a pore size of the CPG ranges from 500 angstroms (Å) to 2000 Å.

In a preferred embodiment, the nucleic acid purification device further includes a screen plate. The screen plate includes an upper screen plate and a lower screen plate, and the CPG is disposed between the upper screen plate and the lower screen plate.

In a preferred embodiment, the upper screen plate is hydrophilically treated or selected from hydrophilic materials, and the lower screen plate is selected from hydrophobic materials.

In a preferred embodiment, the solid support further includes a thermoplastic polymer resin, and the thermoplastic polymer resin is sintered with the CPG to form a Controlled Pore Glass Frit (CPG Frit).

In a preferred embodiment, the thermoplastic polymer resin is selected from polyethylene, and preferably ultra-high molecular weight polyethylene (UHMW-PE) or high-density polyethylene (HDPE).

In a preferred embodiment, the CPG Frit has a diameter smaller than or equal to 3.5 mm and a thickness greater than or equal to 1.5 mm.

In a preferred embodiment, the nucleic acid purification device further includes a receiving device, and the solid support is disposed in the receiving device.

In a preferred embodiment, the aforementioned receiving device is a hollow column tube.

In a preferred embodiment, at least one assembly site is provided within the hollow column tube, the assembly site defines a cylinder, the solid support is in a shape of a cylinder, the solid support tangentially fits the assembly site, and a height of the assembly site is greater than a thickness of the solid support.

According to a sixth aspect, an embodiment provides a nucleic acid purification device, which includes the nucleic acid purification device of the fifth aspect.

According to a seventh aspect, an embodiment provides a nucleic acid purification method. The method includes: adding a solution containing a nucleic acid to be purified into the nucleic acid purification device of the fifth aspect for incubation, wherein the nucleic acid to be purified is complementary paired or randomly paired with all of or a part of a fragment of oligonucleotide sequence in the nucleic acid purification device; and eluting the nucleic acids to be purified from the nucleic acid purification device.

In a preferred embodiment, the nucleic acid to be purified is a single-stranded nucleic acid.

In a preferred embodiment, the nucleic acid purification device is subjected to an ammonolysis deprotection treatment prior to the incubation with the solution. In the present disclosure, the aminolysis deprotection treatment refers to, under aminolysis conditions, the removal of a protecting group on amino group of a heterocyclic base of the monomer or multimer used to synthesize the oligonucleotide, as well as the removal of the cyanoethyl protecting group on the hydroxyl group of the phosphoester, to restore the structure of the oligonucleotide itself.

In a preferred embodiment, the ammonolysis deprotection treatment is performed at 90° C. for 2 hours; subsequently, washing is performed with a mobile phase of acetonitrile/water solution and ultrapure water, followed by centrifugation, and the nucleic acid purification device with attached oligonucleotide sequence is obtained and incubated with the solution.

In a preferred embodiment, the incubation is followed by washing with ethanol/water as a mobile phase to remove unbound nucleic acid and/or enzyme and/or buffer, and eluting the nucleic acids to be purified from the nucleic acid purification device.

In a preferred embodiment, said eluting the nucleic acid to be purified from the nucleic acid purification device includes: under a heating condition, denaturing and unwinding the nucleic acid to be purified and the oligonucleotide sequence that are paired; and eluting the unwound single-stranded nucleic acid to be purified with heated ultrapure water.

In a preferred embodiment, the nucleic acid to be purified, after eluted from the nucleic acid purification device, is annealed to restore a double-helical structure of complementary single strands.

According to an eighth aspect, an embodiment provides a use of the nucleic acid purification device of the fifth aspect in nucleic acid purification.

In the nucleic acid synthesis device of the present disclosure, the CPG is a bare CPG that is unmodified, has no universal linker, and has a certain number of hydroxyl groups exposed on the surface, and the nucleic acids such as oligonucleotide primers are synthesized and then subject to the aminolysis treatment, and the nucleic acids such as oligonucleotide primers attached to the CPG are not cleaved and remain attached to the solid support. Thus, the nucleic acid synthesis device of the present disclosure is capable of synthesizing nucleic acids and immobilizing nucleic acids, simultaneously. It can be used not only for the synthesis of nucleic acids such as oligonucleotide primers, but also for the purification of digestion products, PCR products, and the like by using the nucleic acids such as oligonucleotide primers immobilized on CPG, having the advantages of simple structure, small size, light weight, high efficiency, low costs, and diversified functions.

The nucleic acid purification device of the present disclosure is capable of purifying a specific nucleic acid sequence and has the advantages such as efficient, fast, convenient, safe and non-toxic, thereby overcoming the deficiencies that the existing nucleic acid separation and purification methods cannot purify a specific DNA sequence and are complex in operation, inefficient, slow separation speed, high economic cost, and the need to use toxic chemical reagents.

DESCRIPTION OF EMBODIMENTS

The present disclosure is described in detail below in conjunction with the accompanying drawings. In the following detailed description, numerous details are set forth for facilitating the understanding of the present disclosure. However, those skilled in the art will appreciate that some of the features may be omitted or may be replaced by other elements, materials, methods under different circumstances.

Furthermore, features, operations, or characteristics described in the specification can be combined in any appropriate manner to form various implementations. Meanwhile, in a manner obvious to those skilled in the art, steps or actions for describing a method can also be exchanged or adjusted in terms of order. Therefore, the various orders in the specification and the drawings are only for the purpose of clearly describing a certain embodiment, but are not the necessary orders, unless it is otherwise stated that a certain order must be followed.

An embodiment of the present disclosure provides a nucleic acid synthesis device. The device includes a solid support comprising controlled pore glass (CPG), the CPG is an unmodified and bare CPG. A surface thereof does not carry a universal linker with chemical groups, but has hydroxyl groups. The hydroxyl group, as a synthesis initiation point of nucleic acid, is bonded through a covalent bond to the phosphoramidite-protected nucleotide monomer or multimer for synthesis of nucleic acid.

In embodiments of the present disclosure, the covalent bond between the hydroxyl group on the CPG surface and nucleotide can be formed by classic solid-phase phosphoramidite triester method. In contrast to the prior art, the embodiments of the present disclosure employ an unmodified and bare CPG, and the hydroxyl group on the surface thereof acts as a 5'-hydroxyl group in the solid-phase phosphoramidite triester to react and bond to the added phosphoramidite-protected nucleotide monomer or multimer.

The nucleic acid synthesis device of the present disclosure is suitable for the synthesis of any suitable nucleic acids, for example, including but not limited to DNA and RNA, preferably DNA. Thus, in a preferred embodiment, the nucleic acid synthesis device of the present disclosure is a DNA synthesis device.

In the embodiments of the present disclosure, the controlled pore glass (CPG) has many irregular internal pore canals, and has a large pore network. A size of the pore canal is also referred as to a pore size, and the CPG has stable pore size. Generally, CPG having a pore size of 500 Angstroms (Å) to 2000 Å, and preferably 1000 Å, is selected for preparing of nucleic acid synthesis device according to the embodiment of the present disclosure. Other pore sizes can be selected as well. The pore size of the controlled pore glass (CPG) to be used may be determined according to specific conditions.

In embodiments of the present disclosure, nucleic acid synthesis device may be designed in a variety of suitable forms. The present disclosure provides two exemplary forms.

In a first form, a nucleic acid synthesis device includes a controlled pore glass (CPG) and a screen plate. The screen plate includes an upper screen plate and a lower screen plate. The controlled pore glass (CPG) is disposed between the upper screen plate and the lower screen plate. The screen plate may be formed by sintering a thermoplastic polymer resin powder such as ultra-high molecular weight polyethylene (UHMW-PE) or high-density polyethylene (HDPE). The screen plate is configured to block CPG from leaking down and to allow synthesis reagents to pass through. The upper screen plate is hydrophilically treated or selected from hydrophilic materials, and the lower screen plate is selected from hydrophobic materials. In addition, the nucleic acid synthesis device further includes a receiving device, in which the solid support such as the controlled pore glass (CPG) and optionally the screen plate are disposed. The receiving device may be a hollow column tube, which can be molded by injection of polypropylene.

In a second form, a nucleic acid synthesis device includes a Controlled Pore Glass Frit (CPG Frit) as a solid support, which is formed by sintering the controlled pore glass (CPG) with a thermoplastic polymer resin. A temperature for the sintering may be range from 160° C. to 250° C., and preferably 180° C. The thermoplastic polymer resin may be selected from polyethylene, polypropylene, and the like, preferably ultra-high molecular weight polyethylene (UHMW-PE) or high-density polyethylene (HDPE). Polyethylene (PE) particles encase and immobilize CPG. The PE particles are bridged to form a certain pore size, and the CPG is uniformly embedded in a rigid network structure formed by the PE bridges to form the CPG Frit with a certain pore size and porosity. During oligonucleotide sequence synthesis, the synthesis reagent flows through the internal pore canals of CPG and the pore canals formed by the PE bridges, which ensures a sufficient length of the flow path of the reagent, thereby prolonging the duration of the chemical reaction and increasing the opportunity for the reactants to contact reaction sites on the CPG. The CPG spheres are immobilized by the encapsulation effect of the polymer, and thus they cannot be rotated due to the flow of reagent, which further prolongs the contact time between reagent and reaction sites on the CPG, thereby improving synthesis efficiency and product purity. In this form, the CPG Frit has a cylindrical shape, which has any suitable diameter, for example, a diameter ≤3.5 mm; and has any suitable thickness, such as a thickness ≥1.5 mm. Preferably, CPG Frit has a diameter of 3 mm and a thickness of 4 mm. Each CPG Frit contains 0.1-10 mg of CPG, preferably 4 mg of CPG.

Since PE material or other materials used for nucleic acid synthesis are extremely hydrophobic and molecular biological reactions such as PCR reaction are mostly performed in aqueous solution, the hydrophobic materials limit their further application. Through hydrophilic treatment, these materials can absorb an aqueous solution, thereby broadening their application range in the field of synthetic biology. Therefore, in order to improve the hydrophilicity of CPG Frit, CPG Frit can be the CPG Frit that is hydrophilically treated. The hydrophilic treatment includes: wetting with an alcoholic solvent, and then bonding to a surfactant.

The alcoholic solvent may be a C1-10 linear or branched alcoholic solvent, preferably methanol, ethanol, propanol, n-butanol, ethylene glycol, glycerol, and aqueous solvents or combinations thereof, and more preferably 95% (v/v) ethanol. The surfactant can be an anionic surfactant, a cationic surfactant, a zwitterionic surfactant, or a nonionic surfactant, and preferably sodium lauryl sulfate, benzalkonium bromide, polysorbate, fatty acid sorbitan, a quaternized compound, lecithin, amino acid, or a combination thereof.

In some preferred embodiments, the nucleic acid synthesis device of the present disclosure further includes a receiving device, in which the solid support such as the CPG Frit is disposed. The receiving device may be a hollow column tube, which can be molded by injection of polypropylene.

In a preferred embodiment, the receiving device is a hollow column tube, the solid support, i.e., the CPG Frit, has a cylindrical shape and disposed in the hollow column tube. The hollow column tube is provided with at least one assembly site, and the assembly site defines a cylinder having no slope. In this way, the solid support in a cylindrical shape can tangentially fit the hollow column tube, and a height of the assembly site is greater than a thickness of the solid support.

In a preferred embodiment, the hollow column tube is injection molded from polypropylene and adopts a design of straight port with a varying inner diameter, and a reserved assembly site for CPG Frit is in a shape of cylinder with no slope. A column length of the hollow column tube is 70 mm; an inner diameter of the hollow column tube is 4.52 mm at an upper portion of the hollow column tube and reduces to 3 mm at an upper side of the assembly site, and the inner diameter of the hollow column tube is 2.95 mm at the assembly site; and the height of the assembly site is 5 mm.

Furthermore, in the nucleic acid synthesis device of the present disclosure, other suitable formats of the receiving device may be used, in addition to the hollow column tube, for example, a perforated plate such as 24-well plate, 96-well plate, 384-well plate, etc. Each CPG Frit, or CPG and screen plate is/are placed in each well of the perforated plate, to form the nucleic acid synthesis device in a perforated plate format, enabling batch synthesis of nucleic acid.

Figure 1:
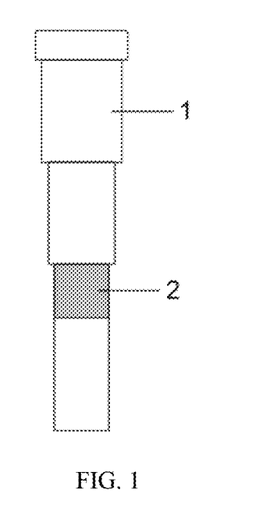
FIG. 1 is a schematic diagram of a design of nucleic acid synthesis column or nucleic acid purification column according to an embodiment of the present disclosure, where 1 denotes hollow column tube; and 2 denotes a CPG Frit fitted inside the hollow column tube.
Figure 2:
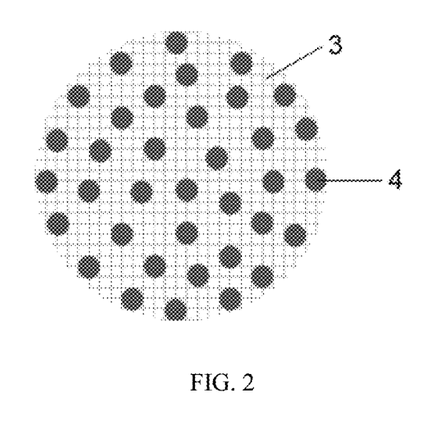
FIG. 2 is a cross-sectional view of a CPG Frit of a nucleic acid synthesis column or a nucleic acid purification column according to an embodiment of the present disclosure, where 3 denotes a rigid network formed by bridges between PE particles; and 4 denotes unmodified and bare CPG sphere without universal linker.
Figure 3:
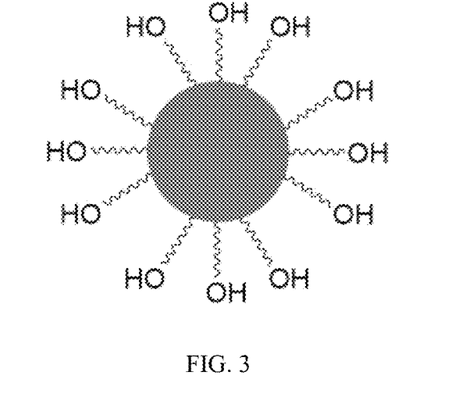
FIG. 3 is a schematic structural diagram of a CPG of a nucleic acid synthesis column according to an embodiment of the present disclosure, where a surface of an unmodified and bare CPG sphere has hydroxyl (—OH) groups.

As shown in FIG. 1, FIG. 2 and FIG. 3, in an exemplary embodiment of the present disclosure, the nucleic acid synthesis device is a nucleic acid synthesis column. The nucleic acid synthesis column includes a hollow column tube 1 and a CPG Frit 2 fitted in the hollow column tube. The CPG is an unmodified and bare CPG support without universal linker, which has a certain number of hydroxyl groups exposed on the surface. The CPG has a pore size of 1000 Å. The CPG Frit 2 is formed by sintering the unmodified and bare CPG spheres 4 with a thermoplastic polymer resin (e.g., PE). The PE particles are bridged to form a rigid network structure 3. A sintering temperature may be in a range of 160° C. to 250° C., preferably 180° C. The sintering time may be 5 minutes to 10 hours, which can be specifically determined as needed. FIG. 3 illustrates that a certain number of hydroxyl groups (—OH) is exposed on a surface of a bare CPG support, and the hydroxyl groups can be bonded, though a covalent bond, to a phosphoramidite-protected nucleotide monomer or multimer to be added.

An embodiment of the present disclosure provides a nucleic acid synthesis apparatus, including a nucleic acid synthesis device according to the embodiments of the present disclosure. In addition to the nucleic acid synthesis device of the present disclosure, the nucleic acid synthesis apparatus of the present disclosure further includes other parts such as a liquid circulation system, a gas circulation system, a control system, a transmission system, etc., which may be implemented according to the related art. As an example of the nucleic acid synthesis apparatus of the present disclosure, the nucleic acid synthesis device used in the Dr. Oligo 192 nucleic acid synthesizer may be replaced with the nucleic acid synthesis device of the present disclosure.

An embodiment of the present disclosure provides uses of the nucleic acid synthesis device of the present disclosure in a method for synthesizing nucleic acids. The synthesized nucleic acid may be any suitable nucleic acid, for example, including but not limited to DNA and RNA, preferably DNA.

In preferred embodiments, the synthesis of nucleic acids is performed using a solid-phase phosphoramidite triester method. For example, the nucleic acid synthesis device according to the present disclosure may be used as a synthesis column in a Dr. Oligo 192 nucleic acid synthesizer, and a fragment of oligonucleotide primer sequence is synthesized on the synthesizer using the classic solid-phase phosphoramidite triester method.

An embodiment of the present disclosure provides a nucleic acid synthesis method using a nucleic acid synthesis device or a nucleic acid synthesis apparatus of the present disclosure in which a hydroxyl group of a CPG surface is used as a point of initiation of synthesis of a nucleic acid to be synthesized to which a phosphoramidite-protected nucleotide monomer or multimer is attached by covalent bonding. In preferred embodiments, the nucleic acid synthesis method is a solid-phase phosphoramidite triester method.

An embodiment of the present disclosure provides a nucleic acid purification device. The device includes a solid support, the solid support includes a controlled pore glass (CPG), and the CPG is an unmodified and bare CPG that has no universal linker and has hydroxyl groups on its surface. The hydroxyl groups are ligated, though a covalent bond, to a fragment of an oligonucleotide sequence, and the fragment of oligonucleotide sequence is specifically complementary paired or randomly paired with all of or a part of a nucleic acid to be purified.

In embodiments of the present disclosure, the covalent bonding between the hydroxyl group on the CPG surface and the oligonucleotide sequence can be achieved by the classic solid-phase phosphoramidite triester method. In contrast to the prior art, the CPG employed in the embodiments of the present disclosure is an unmodified and bare CPG, and the hydroxyl group on the surface thereof acts as a 5'-hydroxyl group in the solid-phase phosphoramidite triester to react and bond with the added phosphoramidite-protected nucleotide monomer or multimer.

In embodiments of the present disclosure, the fragment of oligonucleotide sequence is specifically complementary paired or randomly paired with all of or a part of a nucleic acid to be purified. In this way, the specific nucleic acid sequence can be purified purposefully. When the sequence of the nucleic acid to be purified is known, it is easy to design the above-mentioned oligonucleotide sequence according to the principle of base complementary pairing. In general, the position where the oligonucleotide sequence is paired with the nucleic acid to be purified can be selected to be located at a regional fragment at a 3'-end or/and 5'-end of the nucleic acid to be purified, specifically, a regional fragment at a 3'-end of the nucleic acid to be purified, a regional fragment at a 5'-end of the nucleic acid to be purified, or regional fragments at a 3'-end and 5'-end of the nucleic acid to be purified.

In general, a length of the oligonucleotide sequence is not particularly limited, and any length can be selected according to specific needs. However, according to the experimental results, it is determined that the length of the oligonucleotide sequence within the range of 6 to 12 bases can achieve excellent results, for example, 6 bases, 8 bases, 10 bases, or 12 bases.

In embodiments of the present disclosure, the term "nucleic acid purification device" indicates that the device of the present disclosure can purify any suitable nucleic acid, including but not limited to DNA and RNA. In a preferred embodiment of the present disclosure, the nucleic acid to be purified is DNA, and accordingly, the nucleic acid purification device of the present disclosure is a DNA purification device. In a more preferred embodiment, the nucleic acid to be purified is a biological reaction product, which can be a product from any biological or biochemical reactions, and a particular fragment of the product is required to be purified. The typical but non-limiting examples of the biological reaction products are enzymatic products, PCR products, etc.

In the embodiments of the present disclosure, the CPG has many irregular internal pore canals, and has a large pore network. A size of the pore canal is also referred to as a pore size, and the CPG has stable pore size. Generally, CPG having a pore size of 500 Angstroms (Å) to 2000 Å, and preferably 1000 Å, is selected for preparing of nucleic acid synthesis device according to the embodiment of the present disclosure. Other pore sizes can be selected as well. In specific applications, the pore size of the CPG to be used may be determined according to specific conditions of the nucleic acid to be purified.

In embodiments of the present disclosure, a nucleic acid purification device may be designed in a variety of suitable forms. The present disclosure provides two exemplary forms.

In a first form, the nucleic acid synthesis device includes a CPG and a screen plate. The screen plate includes an upper screen plate and a lower screen plate. The CPG is disposed between the upper screen plate and the lower screen plate. The screen plate may be formed by sintering a thermoplastic polymer resin powder such as ultra-high molecular weight polyethylene (UHMW-PE) or high-density polyethylene (HDPE). The screen plate is configured to block CPG from leaking down and to allow synthesis reagents to pass through. The upper screen plate is hydrophilically treated or selected from hydrophilic materials, and the lower screen plate is selected from hydrophobic materials. In addition, the nucleic acid synthesis device further includes a receiving device, in which the solid support such as the CPG and optionally the screen plate are disposed. The receiving device may be a hollow column tube, which can be molded by injection of polypropylene.

In a second form, the nucleic acid synthesis device includes a Controlled Pore Glass Frit (CPG Frit) as a solid support, which is formed by sintering CPG with a thermoplastic polymer resin. The thermoplastic polymer resin may be selected from polyethylene, polypropylene, and the like, preferably ultra-high molecular weight polyethylene (UHMW-PE) or high-density polyethylene (HDPE). Polyethylene (PE) particles encase and immobilize CPG. The PE particles are bridged to form a certain pore size, and the CPG is uniformly embedded in a rigid network structure formed by the PE bridges to form the CPG Frit with a certain pore size and porosity. In this form, the CPG Frit has a cylindrical shape, which has any suitable diameter, for example, a diameter ≤3.5 mm; and has any suitable thickness, such as a thickness ≥1.5 mm. Preferably, CPG Frit has a diameter of 3 mm and a thickness of 4 mm. In addition, the nucleic acid purification device may further include a receiving device, in which the solid support such as the CPG Frit is disposed. The receiving device may be a hollow column tube, which can be molded by injection of polypropylene. In a preferred embodiment, the receiving device is a hollow column tube, the solid support, i.e., the CPG Frit, has a cylindrical shape and disposed in the hollow column tube. The hollow column tube is provided with at least one assembly site, and the assembly site defines a cylinder having no slope. In this way, the solid support in a cylindrical shape can tangentially fit the hollow column tube, and a height of the assembly site is greater than a thickness of the solid support.

Furthermore, in the nucleic acid synthesis device of the present disclosure, other suitable formats of the receiving device may be used, instead of the hollow column tube, for example, a perforated plate such as 24-well plate, 96-well plate, 384-well plate, etc. Each CPG Frit, or CPG and screen plate is/are placed in each well of the perforated plate, to form the nucleic acid synthesis device in a perforated plate format, enabling batch synthesis of nucleic acid.

Figure 4:
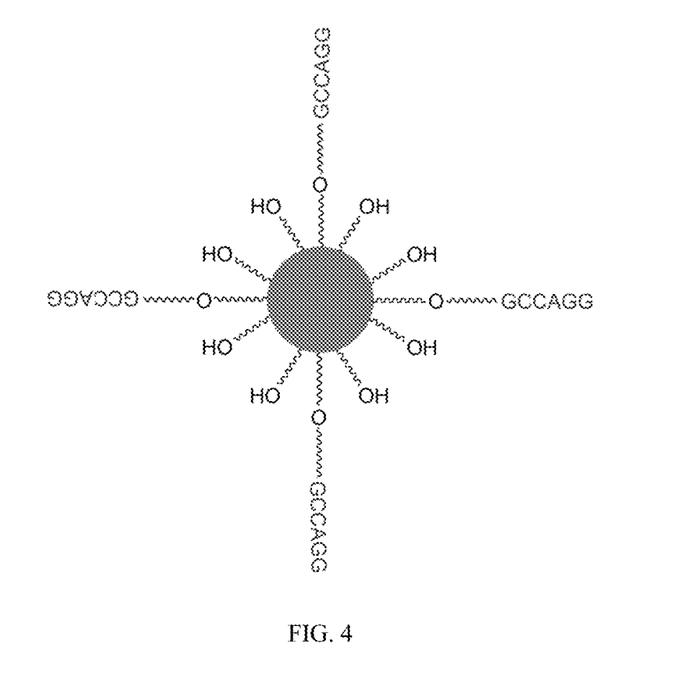
FIG. 4 is a schematic diagram of a CPG structure design of a nucleic acid purification column according to an embodiment of the present disclosure, in which oligonucleotide sequences are attached to a surface of an unmodified and bare CPG sphere.

As shown in FIG. 1, FIG. 2 and FIG. 3, in an exemplary embodiment of the present disclosure, the nucleic acid purification device is a nucleic acid purification column. The nucleic acid synthesis column includes a hollow column tube 1 and a CPG Frit 2 fitted in the hollow column tube. The CPG is an unmodified and bare CPG support without universal linker, which has a certain number of hydroxyl groups exposed on the surface. The CPG has a pore size of 1000 Å. The CPG Frit 2 is formed by sintering the unmodified and bare CPG spheres 4 with a thermoplastic polymer resin (e.g., PE). The PE particles are bridged to form a rigid network structure 3. A sintering temperature may be in a range of 160° C. to 250° C., preferably 180° C. The sintering time may be 5 minutes to 10 hours, which can be specifically determined as needed. FIG. 4 illustrates that a certain number of hydroxyl groups (—OH) is exposed on a surface of a bare CPG support, and the hydroxyl groups can be bonded, though a covalent bond, to a fragment of an oligonucleotide sequence, and the fragment of oligonucleotide sequence is specifically complementary paired or randomly paired with all of or a part of a nucleic acid to be purified.

In a preferred embodiment, CPG Frit is formed by uniformly mixing CPG and UHMW-PE powders and then sintering 180° C., and a diameter of the CPG Frit is 3 mm and the thickness of the CPG Frit is 4 mm. The CPG Frit is subjected to a hydrophilic treatment. A content of CPG in each CPG Frit is 4 mg. The hydrophilic treatment of CPG Frit can include: wetting with alcoholic solvent, and then bonding with surfactant. The alcoholic solvent may be a C1-10 linear or branched alcoholic solvent, preferably methanol, ethanol, propanol, n-butanol, ethylene glycol, glycerol, and aqueous solvents or combinations thereof, more preferably 95% (v/v) ethanol. The surfactant can be an anionic surfactant, a cationic surfactant, a zwitterionic surfactant, or a nonionic surfactant, and preferably sodium lauryl sulfate, benzalkonium bromide, polysorbates, fatty acid sorbitan, a quaternized compound, lecithin, amino acid, or combinations thereof. The hollow column tube can be injection molded with polypropylene, and adopts a design of straight port with a varying diameter, and a reserved assembly site for CPG Frit is in a shape of cylinder with no slope. A column length of the hollow column tube is 70 mm; an inner diameter of the hollow column tube is 4.52 mm at an upper portion of the hollow column tube and reduces to 3 mm at an upper side of the assembly site, and the inner diameter of the hollow column tube is 2.95 mm at the assembly site; and the height of the assembly site is 5 mm.

An embodiment of the present disclosure provides a nucleic acid purification apparatus, including a nucleic acid purification device according to the embodiments of the present disclosure.

An embodiment of the present disclosure provides a nucleic acid purification method. The method includes: adding a solution containing a nucleic acid to be purified into the nucleic acid purification device of the present disclosure for incubation to allow the nucleic acid to be purified to be complementary paired or randomly paired with a fragment of oligonucleotide sequence in the nucleic acid purification device; and then eluting the nucleic acids to be purified from the nucleic acid purification device.

In embodiments of the present disclosure, the nucleic acid to be purified may be any suitable nucleic acid, including but not limited to DNA and RNA. In a preferred embodiment of the present disclosure, the nucleic acid to be purified is DNA. In a more preferred embodiment, the nucleic acid to be purified is a biological reaction product, which can be a product from any biological or biochemical reactions, and a particular fragment of the product is required to be purified. The typical but non-limiting examples of the biological reaction products are enzymatic products, PCR products, etc.

In embodiments of the present disclosure, the nucleic acid to be purified may contain at least a part of a single-stranded nucleic acid, including but not limited to that the nucleic acid to be purified has a single-stranded protruding end and a double-stranded in the middle, or the nucleic acid to be purified has a double-stranded protruding end and a single-stranded in the middle, or the entire nucleic acid to be purified is a single-stranded. In a preferred embodiment of the present disclosure, the nucleic acid to be purified is a single-stranded nucleic acid.

In a preferred embodiment of the present disclosure, the nucleic acid purification device is subjected to an ammonolysis deprotection treatment prior to incubation with the solution to be purified. For example, the ammonolysis deprotection treatment may be performed at 90° C. for 2 hours; subsequently, washing is performed with a mobile phase of acetonitrile/water solution and ultrapure water, followed by centrifugation, and the nucleic acid purification device with attached oligonucleotide sequence is obtained and incubated with the solution.

Figure 5:
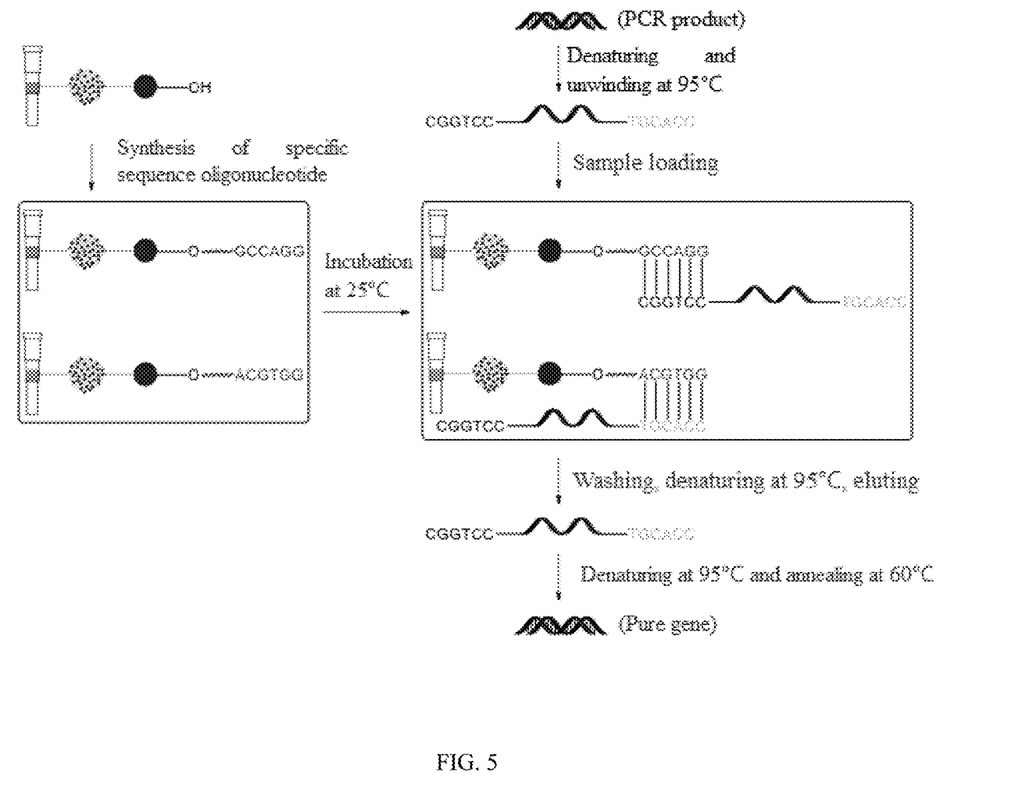
FIG. 5 is a flowchart of a nucleic acid purification method according to an embodiment of the present disclosure.

As shown in FIG. 5, the nucleic acid to be purified is a PCR product. The PCR product is denatured and unwound at high temperature (for example, 95° C.) to form a single strand, each of the both ends of the single strand has a sequence fragment to be complementary paired with the oligonucleotide sequence ligated on the surface of the CPG in the nucleic acid purification device; the denatured and unwound PCR product is loaded into the nucleic acid purification device and incubated, the oligonucleotide sequence ligated to the surface of the CPG is complementary paired with the sequence segment at each of the both ends of the single strand; the unpaired DNAs, enzymes, buffers and other impurities in the reaction system are removed by washing (for example, using ethanol/water solution as mobile phase); then the nucleic acid to be purified is eluted from the nucleic acid purification device, for example, under heating conditions, such that the nucleic acid to be purified and the oligonucleotide sequence are denatured and unwound, and the unwound single-stranded nucleic acid to be purified is eluted with heated ultrapure water; finally, the eluted nucleic acid is denatured and annealed again to restore the double-helical structure of the complementary single-strands to obtain purified DNA product.

An embodiment of the present disclosure provides a use of the nucleic acid purification device of the present disclosure in a purification of nucleic acid, where a fragment of oligonucleotide sequence is ligated to the hydroxyl group on the surface of CPG of the nucleic acid purification device, and the fragment of oligonucleotide sequence is specifically complementary or randomly paired with all or part of the nucleic acid to be purified.

The technical solutions of the present disclosure are described in detail below by way of examples. It should be noted that the examples are merely illustrative and are not to be construed as limiting the scope of protection of the present disclosure.

EXAMPLES

In this example, the specific experimental procedures and steps of the nucleic acid purification method are as follows:

(1) The classic solid-phase phosphoramidite triester method was employed on a Dr. Oligo 192 nucleic acid synthesizer. A fragment of purified "bait" sequence (i.e., degenerate oligonucleotide sequence), which can be randomly paired with DNA to be purified, was synthesized using a hydrophilic DNA synthesis column, in which a CPG Frit was disposed. The CPG Frit included a bare CPG support, and a certain number of hydroxyl groups was exposed on the surface of the bare CPG support. The synthesized degenerate oligonucleotides had sequence lengths of Ent, 8nt, 10nt, 12nt, respectively, and were ligated to CPG Frit, so as to obtain a required DNA purification column.

(2) After the obtained DNA purification column was subjected to ammonolysis deprotection treatment at 90° C. for 2 hours, 400 μl of acetonitrile/water (in a volume ratio of 90:10) and 300 μm of ultrapure water were used as mobile phases to wash, and then centrifuged to obtain a DNA purification column having pure degenerate oligonucleotide sequences attached thereto.

(3) 25 μl of a DNA product solution containing a target fragment of 350 bp in size was obtained by PCR amplification, and heated at 95° C. for 5 minutes to denature and unwind into single strands.

(4) The denatured DNA aqueous solution obtained in step (3) was rapidly loaded into the DNA purification column, absorbed by the CPG Frit, and incubated at 25° C. for 5 minutes to bind to oligonucleotides on the column.

(5) The unbound DNA and other impurities were removed by washing twice with 400₄, of ethanol/water (in a volume ratio of 80:20) as a mobile phase and then centrifuging.

(6) The denaturing and unwinding were carried out by heating at 95° C. for 5 minutes, the unwound single-stranded DNA was eluted with 20 μL of 95° C. ultrapure water, centrifuged and collected.

(7) The DNA aqueous solution obtained in step (6) was heated again at 95° C. for 5 minutes to denature.

(8) After cooling to 60° C. and annealing for 10 minutes, a pure PCR product was obtained.

The purified PCR product was detected with a NanoDrop ultraviolet spectrophotometer, and an $OD_{260}/OD_{280}$ ratio was 1.8 to 2.0.

The following Table 1 shows the comparison results of purification effects of DNA purification columns ligated with oligonucleotides of different lengths (which are all random sequences of degenerate base N) under the same conditions.

TABLE 1

| PCR product concentration (ng/μL) | $OD_{260}/OD_{280}$ | Length of degenerate oligonucleotide sequence (nt) | Concentration after purification (ng/μL) | $OD_{260}/OD_{280}$ after purification |
|---|---|---|---|---|
| 99.4 | 1.91 | 6 | 62.9 | 1.95 |
| 98.3 | 1.88 | 8 | 57.8 | 1.87 |
| 79.6 | 1.93 | 10 | 49.8 | 1.85 |
| 80.5 | 1.87 | 12 | 61.6 | 1.92 |

Figure 6:
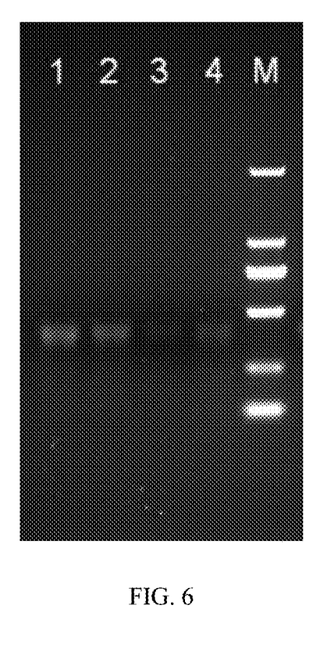
FIG. 6 is a diagram illustrating the results of electrophoresis on a 1.2% agarose gel of DNA fragments obtained by a purification according to an embodiment of the present disclosure, where 1 denotes a PCR product recovered by using a DNA purification column ligated with 6nt degenerate oligonucleotide sequences; 2 denotes a PCR product recovered by using a DNA purification column ligated with 8nt degenerate oligonucleotide sequences; 3 denotes a PCR product recovered by using a DNA purification column ligated with 10nt degenerate oligonucleotide sequences; 4 denotes a PCR product recovered by using a DNA purification column ligated with 12nt degenerate oligonucleotide sequences; and M denotes DL2000 DNA Marker.

FIG. 6 is a diagram illustrating the results of electrophoresis on a 1.2% agarose gel of DNA fragments obtained by the purification according to the above example of the present disclosure, where Lane 1 denotes a PCR product recovered by using a DNA purification column ligated with 6nt degenerate oligonucleotide sequences; Lane 2 denotes a PCR product recovered by using a DNA purification column ligated with 8nt degenerate oligonucleotide sequences; Lane 3 denotes a PCR product recovered by using a DNA purification column ligated with 10nt degenerate oligonucleotide sequences; Lane 4 denotes a PCR product recovered by using a DNA purification column ligated with 12nt degenerate oligonucleotide sequences; and M denotes DL2000 DNA Marker.

From the results in FIG. 6 and Table 1, it can be seen that, by using the nucleic acid synthesis device ligated with a degenerate oligonucleotide sequence according to the present disclosure, based on the complementary pairing relationship between the oligonucleotide sequence and the nucleic acid to be purified, the digestion and PCR products can be quickly and efficiently purified, thereby significantly shortening the purification time; the obtained DNA fragments are detected by an ultraviolet spectrophotometer, and the ratio of OD260/OD280 can be 1.8 to 2.0. The purified DNA product has high purity, and the purification recovery rate is about 50%.

The present disclosure is explained with the above specific examples, which are merely intended to facilitate the understanding of the present disclosure and are not intended to limit the present disclosure. Those skilled in the art, to which the present disclosure pertains, can make several simple developments, modifications or alternatives based on the concept of the present disclosure.

What is claimed is:

1. A nucleic acid purification method, comprising:
adding a solution containing a nucleic acid to be purified into a nucleic acid purification device for incubation, the nucleic acid purification device comprising a solid support, wherein the solid support comprises a controlled pore glass (CPG), the CPG is an unmodified and bare CPG, a surface of the CPG has a hydroxyl group, and the hydroxyl group is covalently bonded directly to an oligonucleotide sequence, and wherein the nucleic acid to be purified is complementary hybridized or randomly hybridized with all of or a part of the fragment of oligonucleotide sequence in the nucleic acid purification device;
eluting the nucleic acids to be purified from the nucleic acid purification device.

2. The nucleic acid purification method according to claim 1, wherein the fragment of oligonucleotide sequence is specifically complementary hybridized or randomly hybridized with all of or part of a regional fragment at a 3'-end or/and 5'-end of the nucleic acid to be purified.

3. The nucleic acid purification method according to claim 1, wherein the nucleic acid to be purified is DNA, and the nucleic acid purification device is a DNA purification device.

4. The nucleic acid purification method according to claim 1, further comprising a screen plate, wherein the screen plate comprises an upper screen plate and a lower screen plate, and the CPG is disposed between the upper screen plate and the lower screen plate.

5. The nucleic acid purification method according to claim 4, wherein the upper screen plate is hydrophilically treated or selected from hydrophilic materials, and the lower screen plate is selected from hydrophobic materials.

6. The nucleic acid purification method according to claim 1, wherein the solid support further comprises a thermoplastic polymer resin, and the thermoplastic polymer resin is sintered with the CPG to form a Controlled Pore Glass Frit (CPG Frit).

7. The nucleic acid purification method according to claim 1, wherein the nucleic acid purification device further comprises a receiving device, and wherein the solid support is disposed in the receiving device.

8. The nucleic acid purification method according to claim 7, wherein the receiving device is a hollow column tube.

9. The nucleic acid purification method according to claim 8, wherein at least one assembly site is provided within the hollow column tube, the assembly site defines a cylinder, the solid support is in a shape of a cylinder, the solid support tangentially fits the assembly site, and a height of the assembly site is greater than a thickness of the solid support.

10. The nucleic acid purification method according to claim 1, wherein the nucleic acid to be purified is a single-stranded nucleic acid.

11. The nucleic acid purification method according to claim 1, wherein the nucleic acid purification device is subjected to an ammonolysis deprotection treatment prior to the incubation with the solution.

12. The nucleic acid purification method according to claim 1, wherein the incubation is followed by washing with a mixture of ethanol and water as a mobile phase to remove unbound nucleic acid and/or enzyme and/or buffer, and eluting the nucleic acids to be purified from the nucleic acid purification device.

* * * * *